(12) United States Patent
Howgill (10) Patent No.: US 10,806,872 B2
(45) Date of Patent: Oct. 20, 2020

(54) DOSE COUNTER FOR METERED DOSE INHALER

(71) Applicant: KINDEVA DRUG DELIVERY L.P., St. Paul, MN (US)

(72) Inventor: Stephen J. Howgill, Thurcaston (GB)

(73) Assignee: KINDEVA DRUG DELIVERY L.P., St. Paul, MN (US)

( * ) Notice: Subject to any disclaimer, the term of this patent is extended or adjusted under 35 U.S.C. 154(b) by 879 days.

(21) Appl. No.: 15/301,125

(22) PCT Filed: Mar. 31, 2015

(86) PCT No.: PCT/US2015/023610
§ 371 (c)(1),
(2) Date: Sep. 30, 2016

(87) PCT Pub. No.: WO2015/153624
PCT Pub. Date: Oct. 8, 2015

(65) Prior Publication Data
US 2017/0021117 A1  Jan. 26, 2017

(30) Foreign Application Priority Data

Apr. 3, 2014 (GB) .................................. 1406047.9

(51) Int. Cl.
*A61M 15/00* (2006.01)
*G06M 1/16* (2006.01)
(52) U.S. Cl.
CPC ...... *A61M 15/0073* (2014.02); *A61M 15/009* (2013.01); *G06M 1/163* (2013.01); *G06M 1/166* (2013.01)
(58) Field of Classification Search
CPC .......... A61M 15/0075; A61M 15/0073; A61M 15/009; A61M 15/0068; G06M 1/04;
(Continued)

(56) References Cited

U.S. PATENT DOCUMENTS 5,881,719 A * 3/1999 Gottenauer ....... A61M 15/0045
128/203.15
6,752,153 B1  6/2004 Eckert
(Continued)

FOREIGN PATENT DOCUMENTS

CH        336211      2/1959
WO   WO 1998-52634  11/1998
(Continued)

OTHER PUBLICATIONS

International Search Report for PCT International Application No. PCT/US2015/023610, dated Jun. 17, 2015, 3 pages.

*Primary Examiner* — Timothy A Stanis
*Assistant Examiner* — Jonathan S Paciorek
(74) *Attorney, Agent, or Firm* — Mueting Raasch Group (57) ABSTRACT

The present disclosure relates to a dose indicator comprising, a chassis comprising a chassis frame and a displacement portion comprising a drive part to engage an indexable first display unit indexable about a first display axis, the indexable first display unit comprising a drive tooth to drive an indexable second display unit indexable about a second display axis, the second display axis being non-coaxial with the first display axis, the indexable second display unit comprising two or more second display unit indexing teeth, wherein the drive tooth and each of the second display unit indexing teeth comprise lips on their respective engagement surfaces, the drive tooth lip and second display unit indexing tooth lip each being adapted to engage at an engagement angle that produces a resultant force acting to pull the first display unit and second display unit together. The present disclosure further relates to an actuator for an inhaler, wherein the actuator comprises a dose indicator as described above. The present disclosure is also directed to an inhaler comprising such actuator.

30 Claims, 9 Drawing Sheets

(58) Field of Classification Search
CPC ...... G06M 1/042; G06M 1/041; G06M 1/045; G06M 1/163; G06M 1/166
See application file for complete search history.

(56) References Cited

U.S. PATENT DOCUMENTS

| | | | | |
|---|---|---|---|---|
| 2006/0060192 A1* | 3/2006 | Lu | ........................ | A61M 15/009 128/200.23 |
| 2007/0210102 A1* | 9/2007 | Stradella | ............... | G06M 1/041 222/36 |
| 2009/0173346 A1* | 7/2009 | Stuart | ................. | A61M 15/009 128/203.12 |
| 2010/0313884 A1* | 12/2010 | Elliman | .............. | A61M 15/009 128/203.12 |

FOREIGN PATENT DOCUMENTS

| WO | WO 2007-124406 | 11/2007 |
|---|---|---|
| WO | WO 2011-071788 | 6/2011 |
| WO | WO 2014-039367 | 3/2014 |
| WO | WO 2015-006292 | 1/2015 |

\* cited by examiner

DOSE COUNTER FOR METERED DOSE INHALER

CROSS REFERENCE TO RELATED APPLICATIONS

This application is a national stage filing under 35 U.S.C. 371 of PCT/US2015/023610, filed Mar. 31, 2015, which claims the benefit of UK Application No. 1406047.9, filed Apr. 3, 2014, the disclosure of which is incorporated by reference in its/their entirety herein.

The present specification relates to dose indicators or dose counters, and more particularly to dose indicators or dose counters for pressurised metered dose inhaler (pMDI) devices. The present invention also relates to actuators comprising such dose indicators/counters and to inhalers comprising such actuators.

Patients who need to use inhalers, such as pMDI devices, need to monitor their inhaler usage, and regulators of medicines have begun to require that some method of dose counting is included into the inhaler. Dose counters (providing a precise count of the number of doses remaining) and dose indicators (providing an indication of the number of doses remaining) for inhalers are known.

In most dose counters and dose indicators, the display is indexed each time the inhaler device is used and a dose is delivered, e.g. from a metering valve of the inhaler where the inhaler is a pMDI. It is particularly important that dose counters and dose indicators do not undercount the number of dispensed doses as, in extreme cases, the patient may rely on the display shown on the pMDI device to receive life-saving medication. Note that the term 'dose', as used herein, includes individual deliveries of medication formulation that in multiple make up a single therapeutic dose.

In dose counters or dose indicators, it may be acceptable for advancement of the display to be triggered (initiated) before or after the dose has been delivered, provided that the patient cannot dispense a dose without triggering it. Many dose counters and/or dose indicators are complex, requiring a number of small mechanical parts, which may increase cost, may lead to difficulties in assembly, and may require tight dimensional tolerances.

WO-A-2011/071788 discloses dose counters for dispensers and in particular dose counters for use with metered dose inhalers.

U.S. Pat. No. 6,752,153 discloses an inhaler for aerosolization of medicament with a dose counter. The dosage counter has a first and a second counting ring and a coupling device that connects the counting rings.

WO-A-98/52634 discloses a dosing device and in particular relates to dosing devices for drug delivery such as injectors and inhalers and a mechanism for use in such devices.

It would be advantageous to provide a dose indicator or dose counter that has fewer essential parts and that is robust and reliable.

In this specification, the term "dose indicator" is intended to refer to both dose counter devices and dose indicator devices.

In a first aspect, there is provided a dose indicator comprising, a chassis comprising a chassis frame and a displacement portion comprising a drive part to engage an indexable first display unit indexable about a first display axis, the indexable first display unit comprising a drive tooth to drive an indexable second display unit indexable about a second display axis, the second display axis being non-coaxial with the first display axis, the indexable second display unit comprising two or more second display unit indexing teeth, wherein the drive tooth and each of the second display unit indexing teeth comprise lips on their respective engagement surfaces, the drive tooth lip and second display unit indexing tooth lip each being adapted to engage at an engagement angle that produces a resultant force acting to pull the first display unit and second display unit together.

This is advantageous because it provides a dose indicator/counter that has a small number of components yet is effective, reliable and compact. Furthermore, because the first and second display units more reliably interact, the invention allows the provision of a cheap, simple and reliable dose-by-dose counter that is capable of counting many (e.g. 100's) doses or inhaler actuations ('puffs'). It may count down from 200 to 0 and is able to fit within a pMDI actuator of similar shape and comparable size to existing actuators.

Usually, the engagement angle is an angle between a line along the engagement direction and a line along a radial axis extending towards the centre of rotation of the first display unit from the point of contact or region of contact between the teeth. The engagement direction is generally taken as the direction from the drive tooth to the second display unit indexing tooth that it drives, along a line orthogonal to the contacting surfaces of these teeth. The engagement angle will often be an acute angle. The engagement angle is often in the range of 85° to 25°, more often in the range 75° to 35°, most often in the range 70° to 40° and usually about 45°.

In most embodiments, the displacement portion may be mounted to the chassis frame by hinge means, preferably at least one hinge. The proximal part of the drive pawl will usually be located on the displacement portion at a position remote from the hinge means or hinges, preferably at a position of the displacement portion distal to the hinge means or hinges.

The hinge means (e.g. hinge or hinges) may generally be any connecting portion including such that allows restricted but controlled relative movement of the displacement portion and the chassis frame, including relative rotational and/or translational movement.

Generally, the first display unit and/or the second display unit will be substantially circular in a cross-section (usually a cross section transverse, preferably generally orthogonal, to the first and/or second display axis respectively) and will be rotatably indexable about the first display axis and/or about the second display axis respectively. The term "substantially circular" in this context includes annular or disc-shaped embodiments and polygonal shapes with at least five sides.

Preferably, the drive part is angled into the first display unit, to help secure engagement and to reduce the chance of the drive part unintentionally disengaging from the first display unit.

Preferably, the chassis is moulded as a unitary piece. This is advantageous because it enables the reduction of the number of parts of the dose indicator, with consequent benefits of cost and simplicity of assembly.

It is preferred if the drive part is integrally comprised in the displacement portion.

In preferred embodiments, the drive part comprises a drive pawl.

Usually, the displacement portion will be adapted to be displaced along a displacement path that is preferably at least partly transverse to the first display axis. It is preferred if the displacement path is at least partly arcuate. This may be achieved, for example, if the drive part is located on the displacement portion at a position remote from the hinge or hinges, preferably at a position distal to the hinge or hinges. The hinge or hinges may also be configured for substantially pivotal (rotational) movement of the displacement portion.

Usually, in a pMDI the displacement portion will comprise at least one press member that acts as an interference portion for interference with the inhaler valve during actuation. The press member or members may for example be a press knuckle or press knuckles. It is advantageous if the contact points (e.g. press knuckles) between the valve and the displacement portion comprise multiple points that are radially in different directions from the valve stem, as this helps to compensate for effects of the patient tilting the pMDI medicament-containing canister slightly during actuation. Thus, preferably there are two or more contact points (e.g. press knuckles) distributed on the displacement portion.

The dose indicator will usually further comprise at least a first display non-return means, the first display non-return means being preferably at least partly located on the chassis frame. The non-return means may be for example a frictional non-return means, but in a preferred embodiment the first display non-return means comprises a non-return arm adapted to interact with one or more detents on the first display unit. The detents on the first display unit may be non-return teeth or may, preferably, be indexing teeth.

The chassis preferably further comprises at least one return means. The return means will usually comprise at least one spring. Preferably, the at least one spring comprises a leaf spring, preferably a curved leaf spring. The at least one return means (preferably a curved leaf spring) will usually directly or indirectly connect the displacement portion and chassis frame, preferably at a position remote from the hinge or hinges.

Usually, the first and/or the second display unit will be adapted to index through between 5 and 25 indicia, preferably 8 to 12 indicia.

The dose indicator may comprise a first display unit mounting means for mounting the display unit on the chassis frame so that it is indexable about the first display axis.

The internal profile of the first display unit may include an axle bearing and the chassis may include an axle ('first display unit axle') with an external profile designed to engage closely with the axle bearing to allow relative rotational movement without wobble. This may be achieved by close circumferential engagement of the internal profile of the first display unit axle bearing and the external profile of the first display unit axle over most of the circumference corresponding to positions on the first display unit axle that are axially separated by some distance. This distance is preferably greater than the thickness of the portion of the first display unit that bears indicia.

The first display unit axle may be substantially cylindrical, or it may have cylindrical sections of different diameter, for example with the section closer to the first display unit's indicia having the larger diameter. The first display unit axle may have a lead-in surface at the distal end to facilitate placing of the first display unit. This first display unit axle may be configured to hold the first display unit in position and to prevent its axial translation along the first display unit axle, e.g. by the provision of circumferential detents in the first display unit axle bearing.

Usually, in embodiments of the invention, the first display unit is a units display unit.

Preferably, the second display unit is a tens display unit.

In some embodiments the first display unit has a substantially circular cross section, e.g. a substantially annular cross section, preferably a cross section transverse (more preferably substantially orthogonal) to the first display axis.

In some embodiments the second display unit has a substantially circular cross section, more preferably a substantially annular cross section. It is preferred if the cross section is transverse (more preferably substantially orthogonal) to the second display axis.

In preferred embodiments, the first and/or the second display unit comprises a zero stop means. It is particularly preferred that the second display unit comprises a zero stop means to stop the second display unit from advancing beyond the zero count of the second display unit (e.g. tens display unit) corresponding to a nearly empty inhaler, and the second display unit is preferably further configured to prevent indexing of the first display unit beyond the ensuing zero units count. This configuration of the stop means may be achieved by using positive engagement between the first (e.g. units) display unit and the second (e.g. tens) display unit. In embodiments where the first and/or the second display unit comprises a zero stop means, the drive member may be configured to deflect or collapse to allow continued use of the inhaler after the displayed overall count has reached zero.

Preferably, the zero stop means interacts with a stop feature located on the chassis.

In any embodiments, advantageously the chassis comprises polyoxymethylene (i.e. POM, acetal). The polyoxymethylene is preferably in homopolymer form.

In a second aspect, the invention provides an actuator for an inhaler, the actuator comprising a dose indicator as discussed in the first aspect.

In a third aspect, the invention provides an inhaler comprising an actuator as discussed in the second aspect.

The dose indicator of the present invention is of simple construction, whilst being robust and reliable in its indication of doses. It is suitable for use in a pressurized metered dose inhaler (pMDI) or other dispensing devices (e.g. dry powder inhalers, aqueous pump dispensers) to indicate usage (e.g. number of doses used or number of doses remaining) by means of numbers and/or coloured regions or other indicia in its display. Typically doses are counted downwards, and an indication of when the inhaler canister needs to be replaced may be provided in addition to an indication of the number of doses that have been dispensed.

When adapted for a pMDI, the dose indicator may be of a suitable size and configuration to fit into existing inhaler actuator designs, including breath actuated actuators or actuators with breath coordination means incorporated, without appreciable changes to the dimensions or shape of the existing actuator design. Actuators will typically be provided with a window for viewing the dose indication or count.

So that the present specification may be more completely understood, reference is made to the accompanying drawings in which like elements are given like reference numerals (with the addition of 100 to the numerals of the second embodiment illustrated).

Certain embodiments of this invention relate to a three-component dose indicator for a pMDI. The indicator is designed to be indexed by the displacement generated when a patient actuates a pMDI valve.

Figure 1:
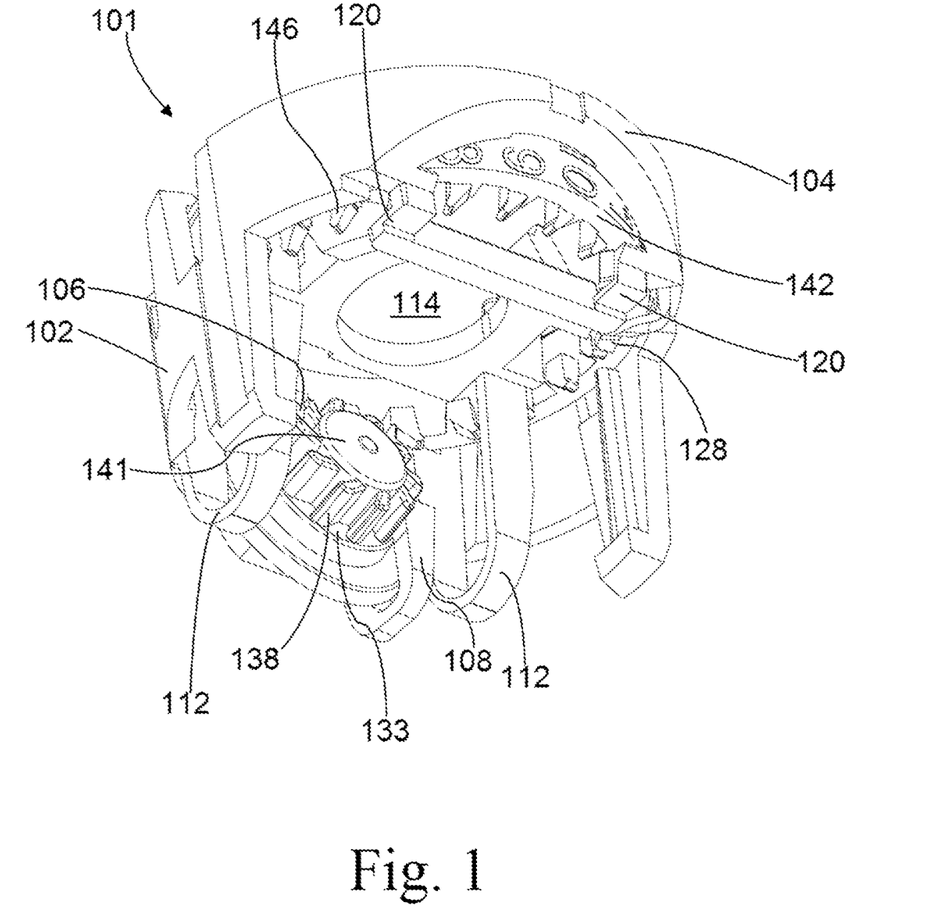
FIG. 1 shows a bottom perspective view of a first exemplary dose indicator.

In FIG. 1, the dose indicator in the form of a dose counter 101 comprises a dose-by-dose counter for a pMDI that is capable of being configured to count down from 200 to 0 and which comprises a chassis 102, a units display unit 133 and a tens display unit 142. These parts are illustrated in exploded form in FIG. 8. The dose counter 101 can be inserted into a standard pMDI actuator.

As shown in FIG. 1, the dose counter 101 comprises a chassis 102 with a chassis frame 104 of generally annular form. The annular form of the chassis frame 104 is designed to fit snugly into an inhaler actuator (shown in FIG. 6) to provide support and to prevent deformation in use. Optionally the support may be enhanced by one or more ledges on the actuator for seating a horizontal surface of the chassis, or ribs/grooves to prevent deformation and relative rotation of the chassis frame in the actuator. Legs 123 are provided on the chassis to secure the dose counter 101 precisely in an actuator body. The chassis 102 incorporates a number of features including springs, hinges and indexing features that are used to actuate and reset the device. The features are formed integrally (i.e. moulded in a unitary piece) with the chassis 102.

The dose counter 101 also comprises a units display unit 133 that comprises a series of units display unit indexing teeth 138. A drive pawl 106 formed integrally with the chassis 102 contacts the indexing teeth 138 and indexes the teeth when the displacement portion of chassis 102 is pressed against by a valve of a medicament canister pressing downwards on indexing knuckles 126 (not visible in FIG. 1; see FIG. 2) on the top side of the chassis 102. When pressed downwards, the displacement portion in the form of displacement plate 119 (see FIG. 2) of the chassis 102 moves downwards and hinges 120, integrally formed with the chassis frame 104 and displacement plate 119, deform. Spring arms 112, also integrally formed with the chassis frame 104 and displacement plate 119, return the chassis 102 to its original position after indexing.

Figure 2:
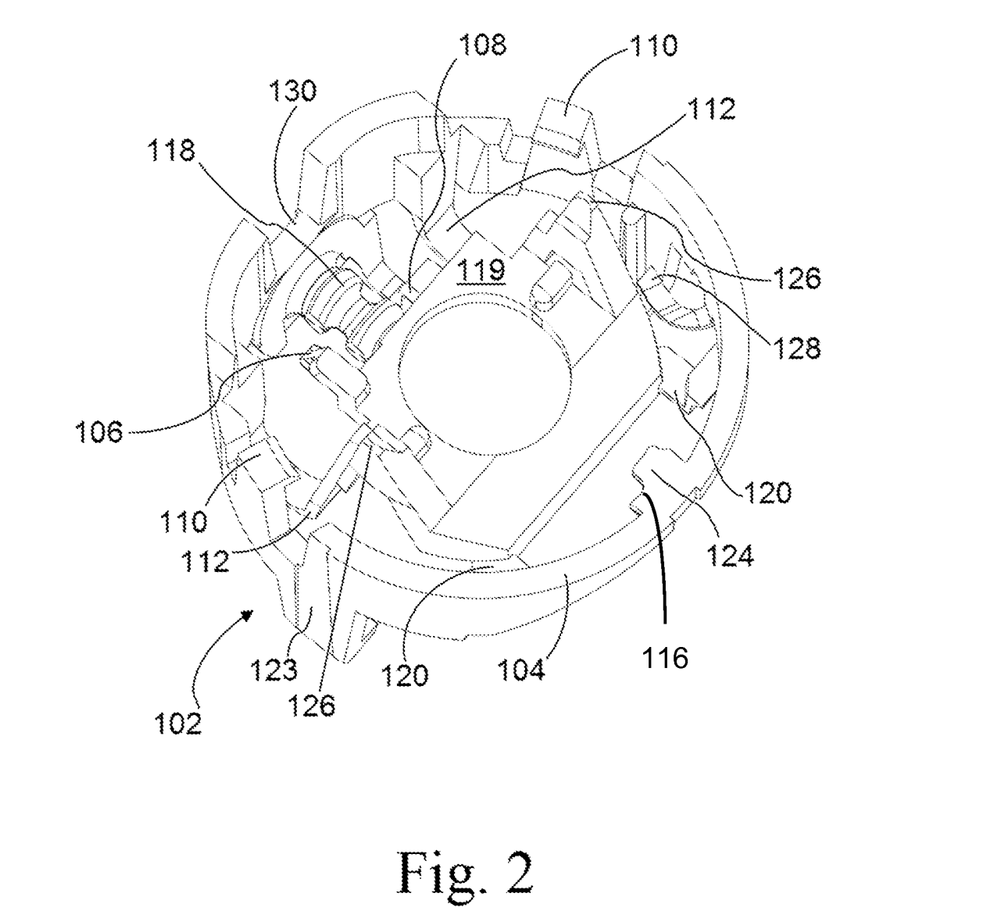
FIG. 2 shows a top perspective view of a chassis of the dose indicator of FIG. 1.

A non-return arm 108, also formed integrally with the chassis 102, contacts the units display unit indexing teeth 138 on the opposite side to the drive pawl 106 and prevents backwards movement of the units display unit 133 and helps urge it into a count-indicating position in which the display indicia are aligned with a window or gap 130 in the chassis (see FIG. 2).

FIG. 2 shows the chassis 102 from a top view. In addition to the features visible in FIG. 1, the chassis 102 comprises indexing knuckles 126 that are contacted by the valve of a medicament canister when it is displaced downwards to actuate the metered dose valve to dispense a metered dose. The indexing knuckles 126 are carried on the displacement plate 119, which is anchored to the chassis frame 104 at one end by two hinges 120 and at the other end by two spring arms 112. An indexing element in the form of the drive pawl 106 is also attached to the displacement plate 119. As discussed above, upon actuation the displacement plate 119 moves downwards and the hinges 120 deform. The spring arms 112 are resilient and resist displacement and return the displacement plate 119 to its original position after actuation. The two spring arms 112 have a long active length in order to reduce stress concentration. This is advantageous because it reduces creep.

Thus, an indexing element is attached to a displacement plate 119 portion that is anchored to a chassis frame 104 at one end by two hinges and at the other end by two spring arms 112 that are also anchored to the chassis frame 104.

Having the spring arms 112 separate from the hinges is also advantageous, as each feature is only required to perform a single function and therefore can be optimised for it.

In alternative embodiments, the hinges could be used to provide the spring force, but due to a short active spring length the stresses and strain in the hinges would be higher.

In an alternative embodiment, the hinge means may be provided by one or more springs.

The chassis frame 104 includes tens display unit clips 110 and tens display unit locating ledge 124 to mount the tens display unit 142, and zero stop feature 116.

The axle bearing 134 (visible in FIG. 8) of the units display unit 133 is mounted on the units display unit axle 118 of the chassis 102, and is located within a hollow boss 141 (FIG. 1) on the units display unit 133. The non-return arm 108 prevents the axial translation of the units display unit 133 along the units display unit axle 118, e.g. it prevents the units display unit 133 jumping off its mounting.

Preferably the drive pawl 106 and non-return arm 108 act at opposite sides of the units display unit axle 118, which allows less stringent tolerance requirements for the axle 118 and axle bearing on the units display unit.

Figure 3A:
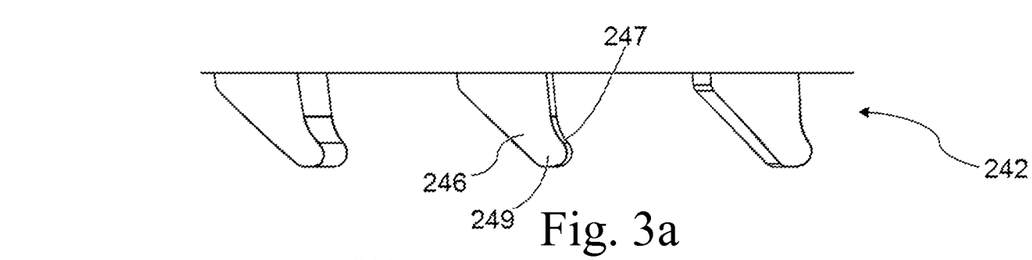
FIGS. 3a and 3b show details of parts of components of a second exemplary dose indicator.
Figure 3B:
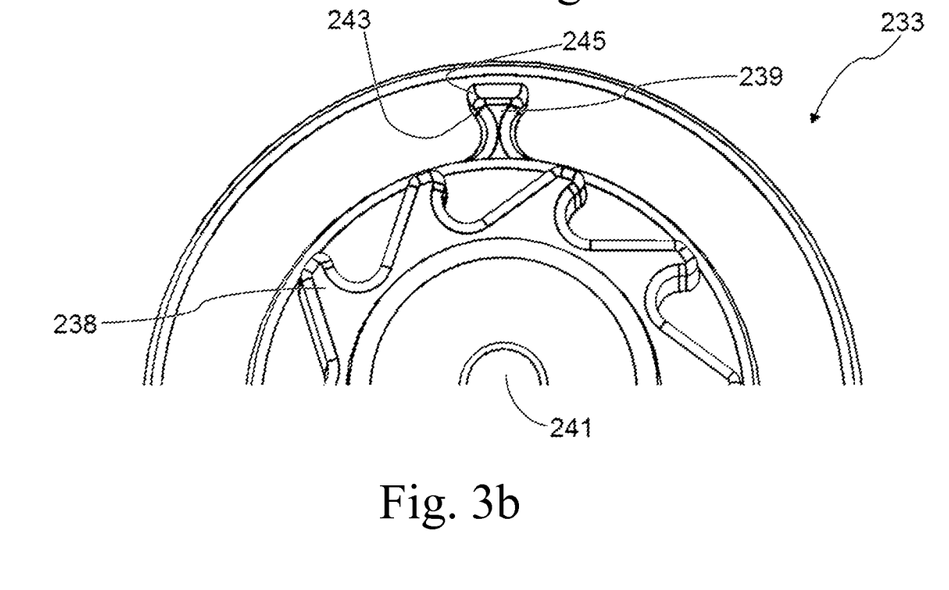
Figure 4:
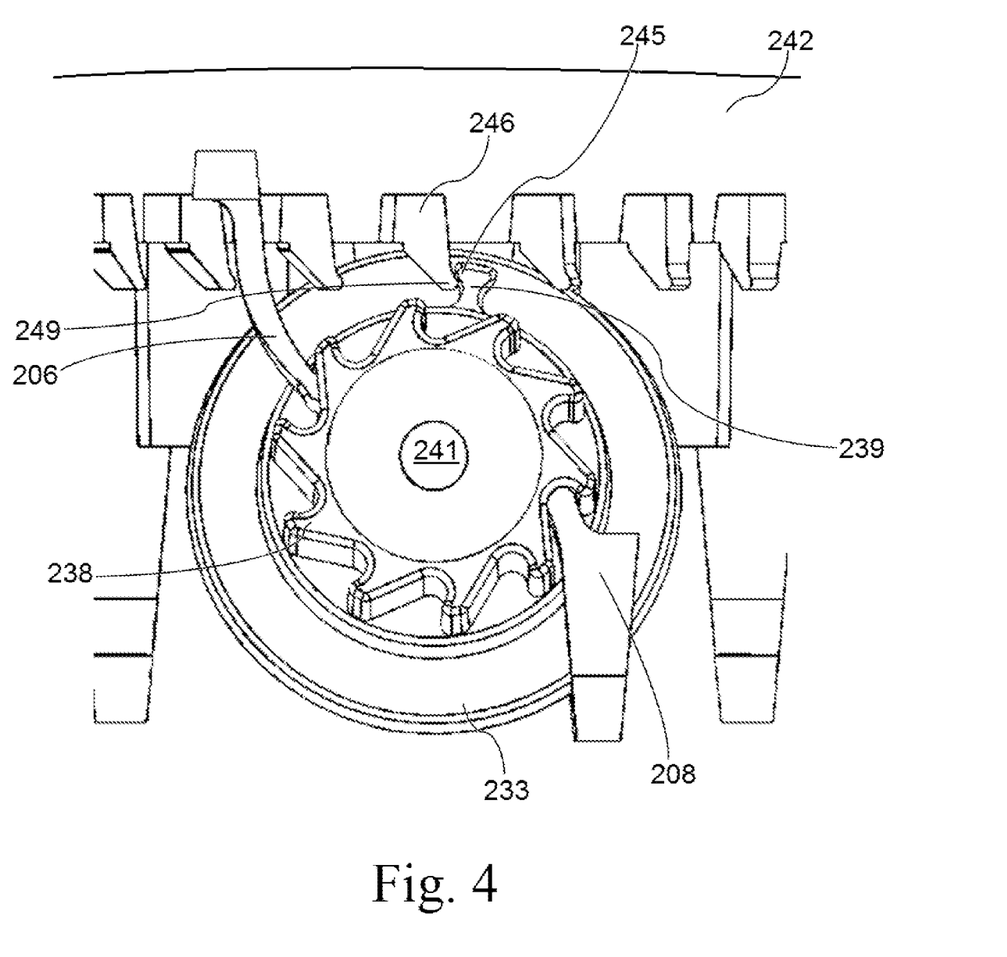
FIG. 4 shows a side view of part of the dose indicator of FIGS. 3a and 3b illustrating its operation.
Figure 5:
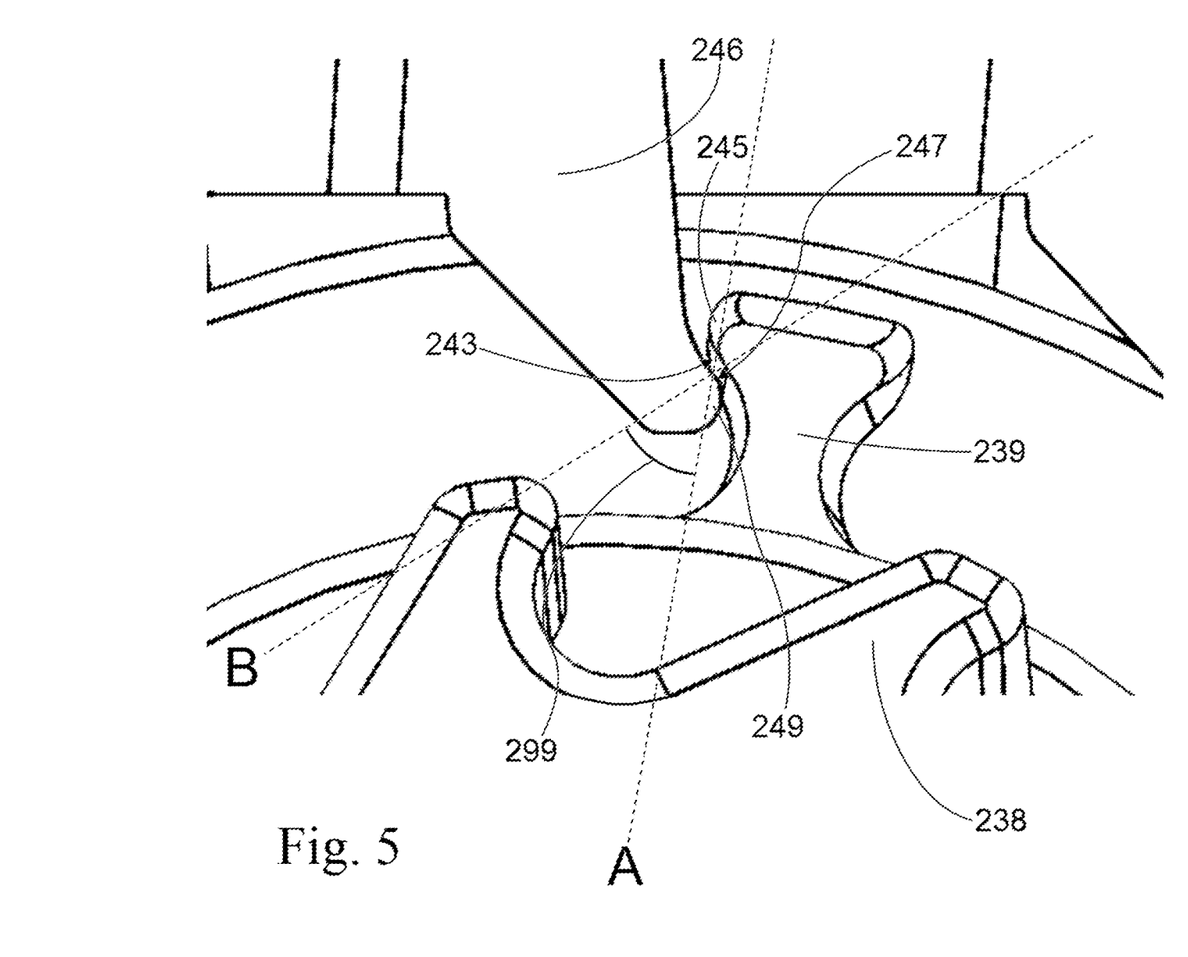
FIG. 5 shows details of the engagement of the drive tooth and tens display unit teeth of the dose indicator of FIGS. 3a, 3b and 4.

The exemplary dose indicator in the form of a dose-by-dose counter of FIGS. 3a-b to 5 is generally similar to that illustrated in FIGS. 1 and 2, and the tens display unit 242 and units display unit 233 described in FIGS. 3a-b to 5 may be used interchangeably in the dose counter of FIGS. 1 and 2.

FIG. 3a shows a view of part of the tens display unit 242, which is a component of generally annular shape. The view includes three tens display unit indexing teeth 246. FIG. 3b shows an axial view of part of the units display unit 233 of an exemplary dose counter from the direction of the units display unit boss 241. The units display unit 233 is mountable on the units display unit axle 218 (see analogous feature 118 in FIG. 2), which is angled at an acute angle with respect to the chassis 202 to take account of the arcuate movement of the drive pawl 206 owing to its position distal to the hinges 220 on the displacement plate 219. The units display unit 233 has an annular array of units display unit indexing teeth 238.

Outside the cylindrical envelope of the units display unit indexing teeth 238, there is a tens display unit drive tooth 239 that, when the tens display unit is fitted to the dose counter, drives the indexing teeth of the tens display unit once per revolution of the units display unit 233. For example, in an embodiment with ten drive teeth 238, the tens display unit would be driven once every 10 actuation cycles.

The tens display unit 242 has a tens display unit display surface (not visible in FIG. 3a) that rotates as the tens display unit 242 is indexed. Although not visible in FIG. 3a, indicia on the surface of the tens display unit may be in the form of a sequence of numerals "20", "19", . . . down to either "00" or "0" or a blank. These numerals, and those of the units indicia, may advantageously be produced by hot foil printing, moulding, embossing, laser marking, or other suitable means. A viewing cut out 230 (see analogous feature 130 in FIG. 2) in the chassis frame 204 of the chassis 202 allows revelation in juxtaposition of the indicia on the tens display unit 242 and those from the units display unit 233, such that together they display the count or indication of doses (e.g. of remaining doses).

The tens display unit 242 has a rim (not visible in FIG. 3a) on its outermost edge which acts as a bearing surface whilst ensuring that the printed display cannot rub against the inside wall of the chassis 202. The tens display unit 242 is located centrally in the chassis 202 by the bearing rim on the outermost surface. It is located axially by a series of clip and location features 210, 224 on the chassis 202.

The tens display unit non-return arm 228 (see analogous feature 128 in FIG. 2) interacts with the tens display unit indexing teeth 246 and prevents rotation in the reverse direction and restricts rotation in the drive direction except when receiving an impulse from the tens display unit drive tooth 239 on the units display unit 233.

Each of the tens display unit indexing teeth 246 has a lip 249 at the end of the tooth to engage the tens display unit drive tooth 239. The lip 249 provides an angled surface 247 that interacts with a corresponding lip on the tens display unit drive tooth 239.

The tens display unit 242 may be injection moulded without the requirement for a side action in the moulding tool. This is advantageous, as it will reduce the capital cost of tooling and reduce the risk of flash on components.

The units display unit 233 has on a face (not visible in FIG. 3b) a units display surface with a plurality (ten numerals 0 to 9 in the illustrated embodiment) of units indicia to indicate the remaining doses.

The tens display unit drive tooth 239 has a drive tooth lip 245 at the end of the tooth to engage each of the tens display unit indexing teeth 246. The drive tooth lip 245 provides an angled surface 243 that interacts with the corresponding angled surface 247 of the lip 249 of each tens display unit indexing tooth 246.

The units display unit 233 has been designed such that it can be injection moulded without the requirement for a side action in the moulding tool. This is advantageous, as it will reduce the capital cost of tooling and reduce the risk of flash on components.

To assemble the dose counter 201, the units display unit 233 is mounted on the units display unit axle 218 on the chassis frame 204. The tens display unit 242 is then hooked under the tens display unit locating ledge 224 and pushed past the two tens display unit clips 210. Once assembled, the dose counter 201 can then be inserted into an actuator as an assembled unit.

FIG. 4 shows part of the exemplary dose counter of FIGS. 3a and 3b part way through actuation. During operation of the dose counter upon actuation of the pMDI valve, the displacement plate bends at its hinges and follows a generally arcuate displacement path. The drive pawl 206 also follows an arcuate path. The drive pawl 206 is angled into the units display unit indexing teeth 238, to further help secure engagement and to reduce the chance of the drive pawl 206 unintentionally disengaging from the units display unit indexing teeth 238. The engagement of the drive pawl 206 with the units display unit indexing teeth 238 advances the display of the units display unit 233 by one count, and the drive pawl 206 then continues its travel as far as it continues to be driven by the user, up to the limit of travel of the pMDI valve. The rotation of the units display unit 233 by one count results in the non-return arm 208 being forced to flex and to ride over the next one of the units display unit indexing teeth 238.

On the return stroke, the spring force of the spring arms 212 causes the drive pawl 206 to return to its original, rest position. The non-return arm 208 engages with the next of the units display unit indexing teeth 238, thus preventing reverse rotation of the units display unit 233. Since the units display unit 233 is unable to rotate, the drive pawl 206 is forced to ride over the next of the units display unit indexing teeth 238 and return to its rest position.

On a tens count (e.g. for a displayed count changing from "190" to "189"), as the dose counter is indexed the rotation of the units display unit 233 causes the tens display unit drive tooth 239 (on the units display unit 233) to engage with one of the tens display unit indexing teeth 246 on the tens display unit 242. The tens unit display unit non-return arm 228 resiliently distorts under the driving force, and once the stroke is completed it detains the tens display unit 242 on the next of the tens display unit indexing teeth 246.

The tens display unit drive tooth 239 engages with the tens display unit indexing teeth 246 so that lip 249 and drive tooth lip 245 interact at an engagement angle. The engagement surfaces are shown in more detail in FIG. 5.

Once the dose counter 201 reaches a display of zero, the zero stop feature 216 on the chassis frame 204 and a zero stop 280 (analogous to zero stop 180 shown in the embodiment of FIG. 8) on the tens display unit 242 come into engagement and prevent further rotation of the tens display unit 242. Interference between the last of the tens display unit indexing teeth 246 and the tens display unit drive tooth 239 on the units display unit 233 in turn prevents the units display unit 233 from rotating further. Due to the resilient flexibility in the chassis 202, spring arms 212 and drive pawl 206, the inhaler can still be actuated once the stop-at-zero features become engaged.

The indexing of the units display unit 233 and tens display unit 242 occurs on the down-stroke of the actuation. This is advantageous, as work on the dose counter 201 is being carried out by the user (rather than, for example, by spring return force, which would be limited). This leads to a more reliable device, as the spring arms 212 need only serve to reset the counter.

Due to the properties required for the spring arms and ratchets, the chassis 202 is preferably made from polyoxymethylene (also known as POM or acetal) or material with similar properties (high stiffness, low friction and good dimensional stability). Preferably the acetal is an acetal homopolymer. POM and materials with similar properties tend to be opaque hence the need for a cut out portion in the chassis and corresponding window in the actuator body so that the indicia are visible.

The chassis component 202 has been designed such that it can be injection moulded without the requirement for a side action in the moulding tool. This is advantageous, as it reduces the capital cost of tooling and reduces the risk of flash on components.

FIG. 5 illustrates the engagement between surfaces 247, 243 of the tens display unit indexing tooth 246 and the tens display unit drive tooth 239 respectively. The lip 249 and drive tooth lip 245 are arranged so that the respective surfaces 247, 243 engage along a line B (i.e. with the transmitted forces, perpendicular to their surfaces at the location of contact engagement, acting along line B) at an engagement angle 299 that is approximately 45° determined with respect to the axis A of the tens display unit drive tooth 239. The axis A is an extension of a radius of the plane (or cross section) of the units display unit 233. Thus, the engagement angle 299 is an angle between a line along the engagement direction (along line B) and a line (line A) along a radial axis extending towards the centre of rotation of the first display unit from the point of contact or region of contact between the teeth. The engagement direction is in this case taken as the direction from the drive tooth 239 to the second display unit indexing tooth 246 that it drives, along a line orthogonal to the contacting surfaces (247, 243 for the drive tooth 239 and second display unit indexing tooth 246 respectively) of these teeth. Since the engagement angle 299 that line B makes with axis A is acute, movement of the tens display unit drive tooth 239 against a tens display unit indexing tooth 249 produces a resultant force along line B that tends to pull components units display unit 233 and tens display unit 242 together, thereby ensuring reliable engagement between them and hence increasing the reliability and robustness of the dose counter. This is particularly important since the components of the dose counter are small and of low mass.

Figure 6:
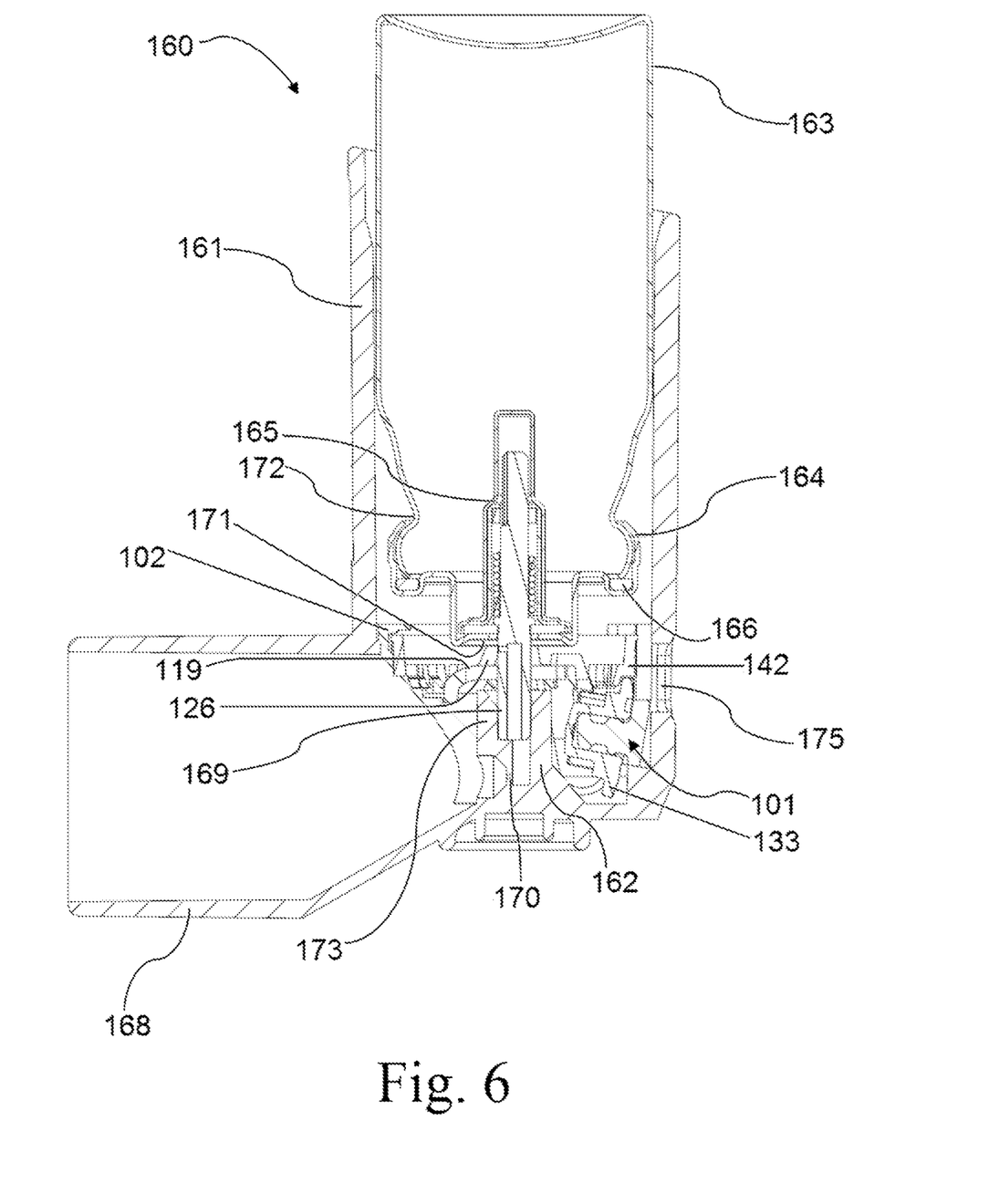
FIG. 6 shows an actuator incorporating the first exemplary dose indicator.

FIG. 6 shows a pressurised metered dose inhaler (pMDI) 160 comprising a canister 163 including a metered dose-dispensing valve 165 mounted via a ferrule 164 on to the neck of a vial 172 component of the canister 163 with an elastomeric gasket 166 to create a seal. The inhaler 160 comprises an actuator 161 including a mouthpiece 168. (In an alternative form, suitable for nasal drug delivery, the actuator may comprise a nosepiece rather than a mouthpiece.) The canister 163 is placed within the actuator 161 by inserting the valve stem 169 of the valve 165, which protrudes outside the ferrule 164, into a stem socket 173 of a stem post 162 of the actuator 161. The valve stem 169 has a dispensing passage that allows for passage of substance from a metering chamber of the valve 165 out through the valve stem 169 and actuator mouthpiece 168 (or nosepiece) to the user. To actuate (fire) the valve 165 to deliver a dose of medicament formulation, the valve stem 169 is pushed inwardly relative to the aerosol container from its resting position, allowing formulation to pass from the canister through the valve 165 and through the actuator nozzle 170 and then out to the patient.

The actuator 161 has a dose indicator in the form of a dose-by-dose counter 101 mounted around the stem post 162. An aperture 114 (see FIG. 1) in the displacement plate 119, larger than the cross-section of the stem post 162, allows for movement of the displacement plate over the stem post. The dose counter 101 has a units display unit 133, a tens display unit 142 and a chassis 102 with a displacement plate 119. During actuation, the canister 163 is pressed down by the user. As the canister 163 is pressed into the actuator 161, the ferrule face 171 surrounding the valve stem 169 contacts indexing knuckles 126 and displaces the displacement plate 119. The result is that the drive pawl (106; not visible in FIG. 6) indexes the units display unit 133. The patient is able to observe the displayed indicia via a window 175 in the actuator 161.

Figure 7A:
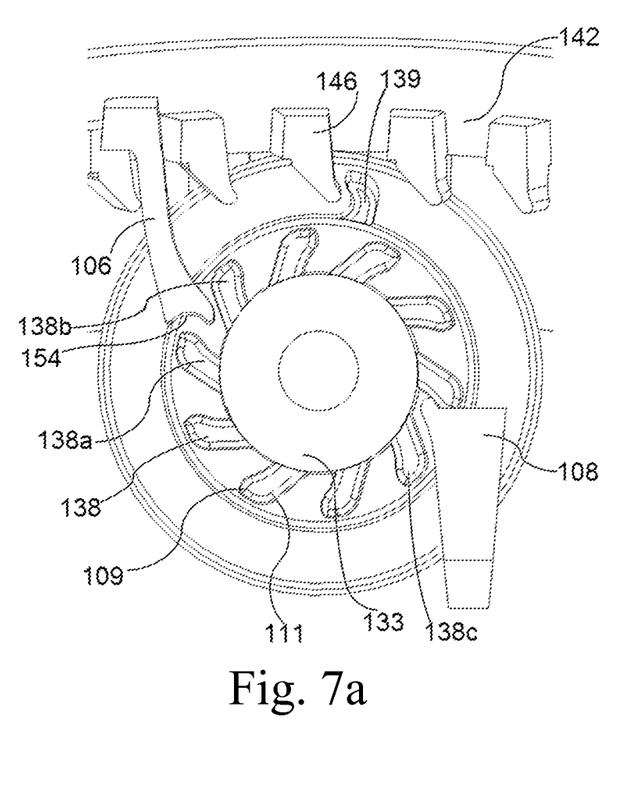
FIGS. 7a and 7b show partial side views of the first exemplary dose indicator, illustrating its operation.
Figure 7B:
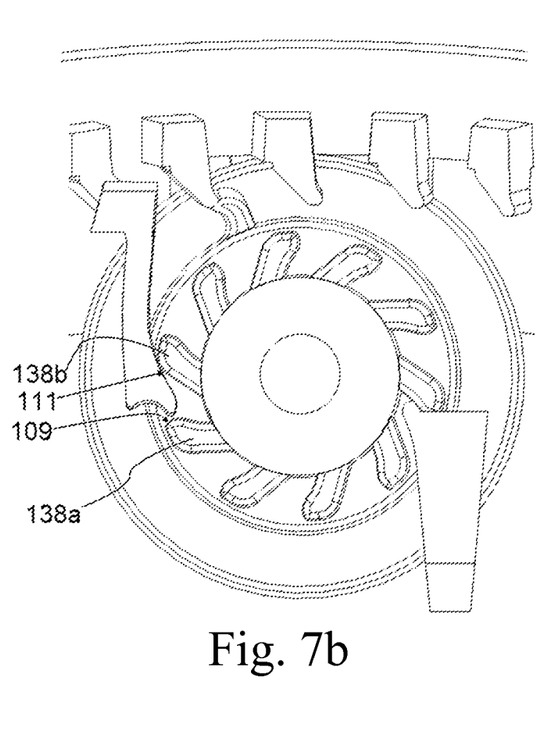

FIGS. 7a and 7b show the exemplary dose counter of FIGS. 1, 2 and 6, FIG. 7a showing the dose counter at rest and FIG. 7b showing it part way through actuation. The dose counter in FIGS. 7a and 7b is similar in most of its components to that illustrated in FIGS. 3a-b to 5, but differs from that illustrated in FIGS. 3a-b to 5 in that the tens display unit drive tooth 139 is non-symmetrical. This provides more clearance from the subsequent tens display unit indexing tooth 146 as it moves into engagement with the previous tooth.

The dose counter in FIGS. 7a and 7b also differs in respect of the shape of the drive pawl 106. The pawl 106 engages the units display unit indexing teeth 138 thereby advancing the display of the units display unit 133 by one count, and the drive pawl 106 then continues its travel as far as it continues to be driven by the user, up to the limit of travel of the pMDI valve. A socket 154 on the drive pawl 106 engages a pawl engaging portion 109 of indexing tooth 138a, which is what causes the rotation of the units display unit 133 by one count and which results in the non-return arm 108 being forced to flex and to ride over an indexing tooth 138c on the opposite side of the units display unit 133. The pawl engaging portion 109 of the indexing tooth is designed to fit snugly in the socket 154 to improve contact during engagement. Once indexed, the patient releases the canister 163 to allow the dose counter 101 to reset under the influence of the spring force from the spring arms (112 in FIG. 1). The non-return arm 108 engages with the next of the indexing teeth 138c, thus preventing reverse rotation of the units display unit 133. Since the units display unit 133 is unable to rotate, the drive pawl 106 is forced to ride over the next of the units display unit indexing teeth 138b and return to its original rest position, resiliently riding over the outer surface 111 of the subsequent indexing tooth 138b. The outer surface 111 of the indexing tooth 138b is shaped to keep the drive pawl's displacement small, and to ensure that its deflection occurs early in its return travel. This avoids the risk of the force from the spring arms 112 being insufficient to ensure that the drive pawl 106 can pass over indexing tooth 138b during its return stroke. This ensures dose counter reliability.

On a tens count (e.g. for a displayed count changing from "190" to "189"), as the counter is indexed the rotation of the units display unit 133 causes the tens display unit drive tooth 139 (on the units display unit 133) to engage with one of the tens display unit indexing teeth 146 on the tens display unit 142. The tens unit display unit non-return arm 128 resiliently distorts under the driving force, and once the stroke is completed it detains the tens display unit 142 on the next of the tens display unit indexing teeth 146.

Figure 8:
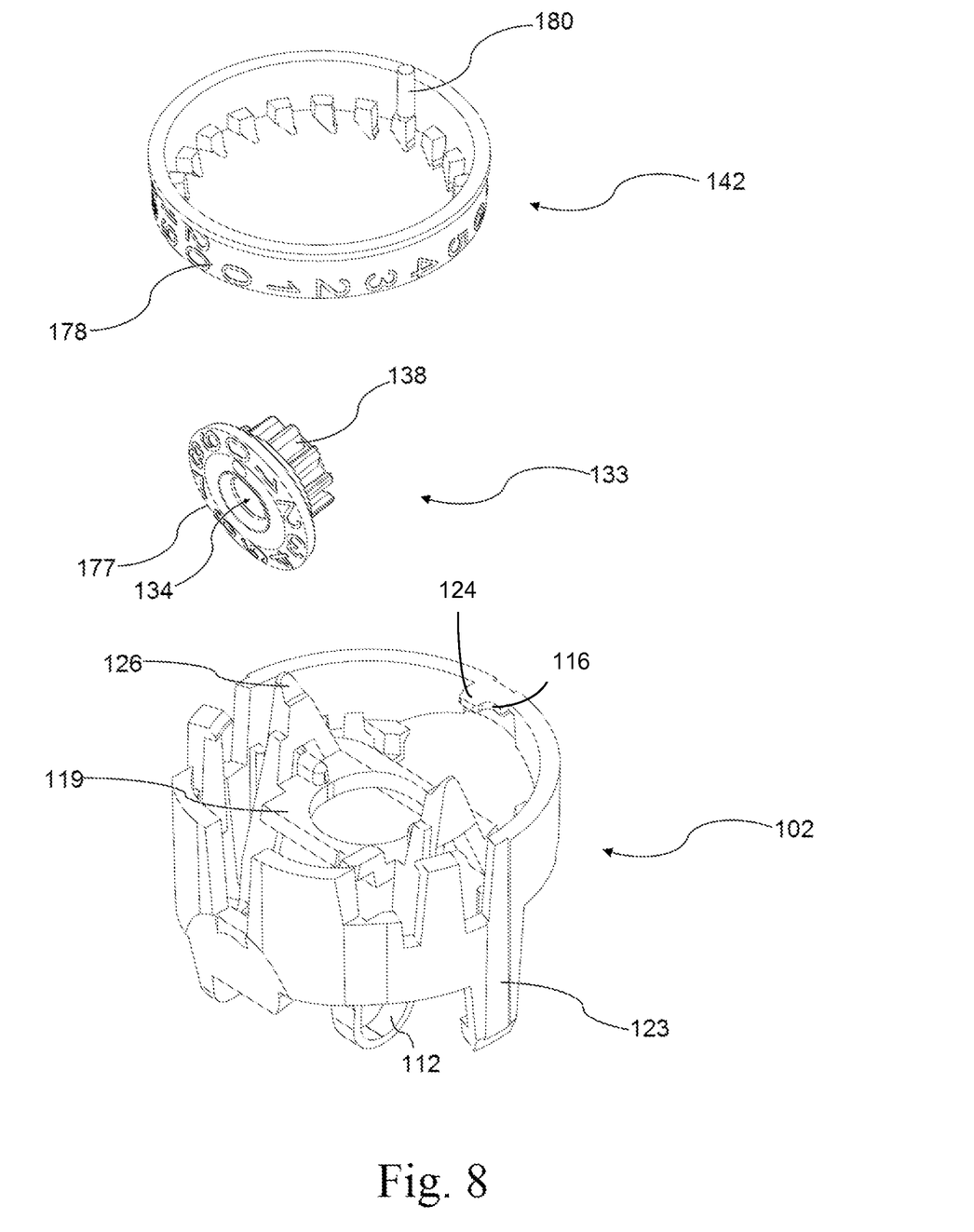
FIG. 8 shows an exploded perspective view of the components of the first exemplary dose indicator.

FIG. 8 shows an exploded view of the three components of the dose indicator in the form of a dose-by-dose counter of FIGS. 1, 2, 6 and 7, and serves to illustrate better some of the features previously discussed. The units display unit 133 is generally circular in external end view with an annular flange providing a units display unit display surface 177 bearing units indicia (e.g. ten numerals 0 to 9). On the internal side of the flange is a series of units display unit indexing teeth 138. In alternative embodiments, the indexing teeth with which the drive pawl interacts may comprise a different set of teeth from the set of indexing teeth with which the non-return arm interacts. FIG. 8 also shows a tens display unit 142 which has a series of tens display unit indexing teeth, each corresponding to an indicium on the tens display unit display surface 178. At one location on the internal surface of the hollow cylinder there is a zero stop means 180 in the form of an attached vertical solid cylindrical protrusion. The zero stop means serves to engage with a stop feature in the form of a corner 116 of the locating ledge 124 on the chassis 102 when the tens display unit 142 has reached its final position at the end of product life. During use, the tens display unit indexing teeth 146 are indexed by the tens display unit drive tooth and generally prevented from backwards movement by the tens display unit non-return arm, best seen in FIG. 9.

Figure 9:
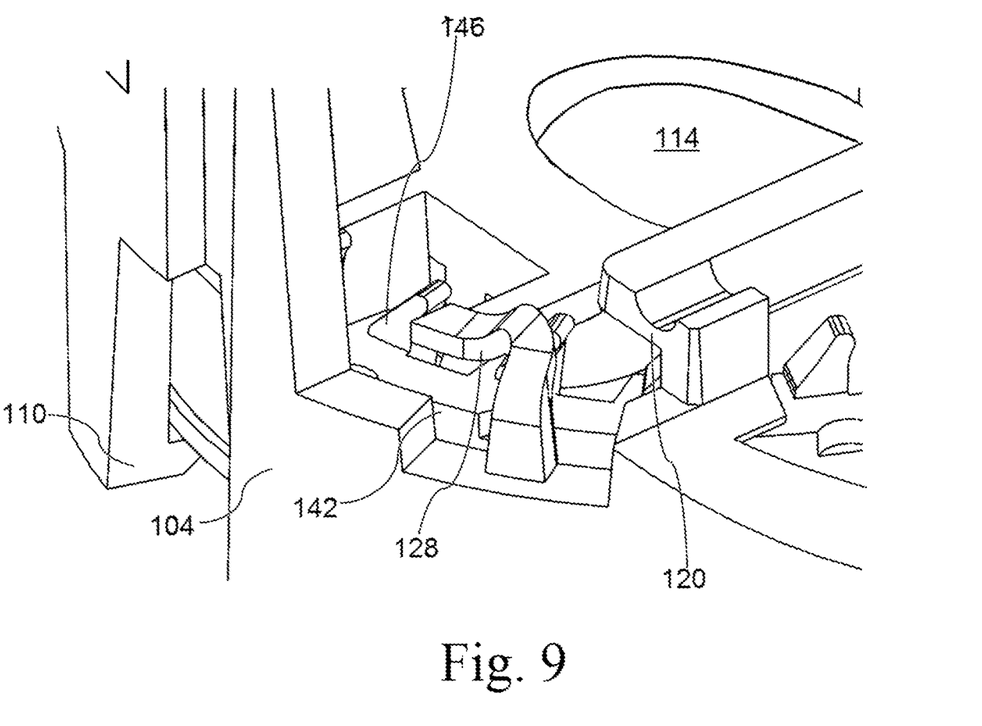
FIG. 9 shows details of the non-return feature for the tens display unit of the first exemplary dose indicator, in an upside down view of part of this dose counter.

FIG. 9 shows the non-return feature for the tens display unit 142. A tens display unit non return arm 128 extends inwardly in an arc from the chassis frame 104, remotely from where the tens display unit drive tooth 139 engages a tens display unit indexing tooth 146. In use, the chisel end of the tens display unit non return arm 128 fits snugly between the lip 149 of a tens display unit indexing tooth and the lower edge (shown in this view as an upper edge) of the tens display unit 142. Thus the indicia displayed through gap 130 are precisely centred due to the positioning of the non-return arm 128 relative to the tooth 146 corresponding to the displayed indicia.

The invention claimed is:

1. A dose indicator comprising, a chassis comprising a chassis frame and a displacement portion comprising a drive part to engage an indexable first display unit indexable about a first display axis, the indexable first display unit comprising a drive tooth to drive an indexable second display unit indexable about a second display axis, the second display axis being non-coaxial with the first display axis, the indexable second display unit comprising two or more second display unit indexing teeth, wherein the drive tooth and each of the second display unit indexing teeth comprise lips on their respective engagement surfaces, the drive tooth lip having a surface facing radially inward that engages a second display unit indexing tooth at an engagement angle such that rotation against each other produces a resultant force acting to pull the first display unit and second display unit together.

2. The dose indicator as claimed in claim 1, wherein the second display axis is transverse to the first display axis.

3. The dose indicator as claimed in claim 1, wherein the engagement angle is an angle between a line along an engagement direction and a line along a radial axis extending towards the centre of rotation of the first display unit from the point of contact or region of contact between the teeth.

4. The dose indicator as claimed in claim 3, wherein the engagement direction is the direction from the drive tooth to the second display unit indexing tooth that it drives, along a line orthogonal to the contacting surfaces of these teeth.

5. The dose indicator as claimed in claim 1, wherein the engagement angle is in the range of 85° to 35°.

6. The dose indicator as claimed in claim 1, wherein the first display unit and/or the second display unit are substantially circular and are rotatably indexable about the first display axis and/or about the second display axis respectively.

7. The dose indicator as claimed in claim 1, wherein the chassis is moulded as a unitary piece.

8. The dose indicator as claimed in claim 1, wherein the drive part is integrally comprised in the displacement portion.

9. The dose indicator as claimed in claim 1, wherein the drive part comprises a drive pawl.

10. The dose indicator as claimed claim 1, wherein the displacement portion is adapted to be displaced along a displacement path.

11. The dose indicator as claimed in claim 10, wherein the displacement path is at least partly transverse to the first display axis.

12. The dose indicator as claimed in claim 1, wherein the drive part is located on the displacement portion at a position remote from a hinge mechanism, at a position distal to the hinge mechanism.

13. The dose indicator as claimed in claim 1, wherein the displacement portion comprises at least one press member.

14. The dose indicator as claimed in claim 1, further comprising at least a first display non-return mechanism, the first display non-return mechanism being at least partly located on the chassis frame.

15. The dose indicator as claimed in claim 14, wherein the first display non-return mechanism comprises a non-return arm adapted to interact with one or more detents on the first display unit.

16. The dose indicator as claimed in claim 1, wherein the chassis further comprises at least one return mechanism.

17. The dose indicator as claimed in claim 16 wherein the return mechanism comprises at least one spring.

18. The dose indicator as claimed in claim 17, wherein the at least one spring comprises a leaf spring.

19. The dose indicator as claimed in claim 16, wherein the at least one return mechanism directly or indirectly connects the displacement portion and chassis frame at a position remote from the hinge mechanism.

20. The dose indicator as claimed in claim 1 wherein the first and/or the second display unit is adapted to index through between 5 and 25 indicia.

21. The dose indicator as claimed in claim 1, further comprising first display unit mounting mechanism for mounting the display unit on the chassis frame so that it is indexable about the first display axis.

22. The dose indicator as claimed in claim 1 wherein the first display unit is a units display unit.

23. The dose indicator as claimed in claim 1, wherein the second display unit is a tens display unit.

24. The dose indicator as claimed in claim 1, wherein the first display unit has a substantially circular cross section.

25. The dose indicator as claimed in claim 1, wherein the second display unit has a substantially annular cross section.

26. The dose indicator as claimed in claim 1, wherein the first and/or the second display unit comprises a zero stop mechanism.

27. The dose indicator as claimed in claim 26, wherein the zero stop mechanism interacts with a stop feature located on the chassis.

28. The dose indicator as claimed in claim 1, wherein the chassis comprises polyoxymethylene.

29. An actuator for an inhaler, the actuator comprising the dose indicator as claimed in claim 1.

30. An inhaler comprising the actuator as claimed in claim 29.

* * * * *